(12) United States Patent
Lee et al.

(10) Patent No.: US 11,529,261 B2
(45) Date of Patent: Dec. 20, 2022

(54) OTITIS MEDIA TREATMENT INSTRUMENT

(71) Applicants: J&KYM CO., LTD., Gimhae-si Gyeongsangnam-do (KR); UNIVERSITY INDUSTRY FOUNDATION, YONSEI UNIVERSITY WONJU CAMPUS, Wonju-si (KR)

(72) Inventors: Hanyoung Lee, Goyang-si Gyeonggi-do (KR); Yong Joon Seo, Wonju-si (KR); Ho Sung Cho, Busan (KR)

(73) Assignee: J&KYM CO., LTD, Wonju-si (KR)

( * ) Notice: Subject to any disclaimer, the term of this patent is extended or adjusted under 35 U.S.C. 154(b) by 331 days.

(21) Appl. No.: 16/651,036

(22) PCT Filed: Sep. 27, 2017

(86) PCT No.: PCT/KR2017/010664
§ 371 (c)(1),
(2) Date: May 29, 2020

(87) PCT Pub. No.: WO2019/066097
PCT Pub. Date: Apr. 4, 2019

(65) Prior Publication Data
US 2020/0390607 A1    Dec. 17, 2020

(30) Foreign Application Priority Data
Sep. 26, 2017 (KR) .................. 10-2017-0124143

(51) Int. Cl.
*A61F 11/20* (2022.01)
*A61M 1/00* (2006.01)

(52) U.S. Cl.
CPC .......... *A61F 11/202* (2022.01); *A61M 1/0023* (2013.01); *A61M 2210/0668* (2013.01)

(58) Field of Classification Search
CPC ..... A61F 11/202; A61F 11/20; A61M 1/0023; A61M 2210/0668; A61M 1/84;
(Continued)

(56) References Cited

U.S. PATENT DOCUMENTS 5,711,309 A * 1/1998 Goldenberg ....... A61B 10/0045
600/583
2005/0266047 A1* 12/2005 Tu ...................... A61F 9/0017
424/427

(Continued)

FOREIGN PATENT DOCUMENTS

CN  2046389 U  10/1989
CN  104519843 A  4/2015
(Continued)

*Primary Examiner* — Adam Marcetich
(74) *Attorney, Agent, or Firm* — Novick, Kim & Lee PLLC; Jae Youn Kim

(57) ABSTRACT

Provided is an otitis media treatment instrument and, more particularly, to an otitis media treatment instrument having a ventilation tube installed thereon, the otitis media treatment instrument including: a cutting sheath which is configured in a tube shape, and which has an inner diameter larger than the outer diameter of the ventilation tube; and a suction pipe formed to be able to move relative to the cutting sheath inside the cutting sheath along the longitudinal direction of the cutting sheath, the suction pipe having, on the front end portion thereof, an insertion portion having an outer diameter smaller than the inner diameter of the ventilation tube and having a fixing portion which extends toward the front end of the insertion portion, and which has an outer diameter larger than the inner diameter of the ventilation tube.

4 Claims, 5 Drawing Sheets

(58) Field of Classification Search
CPC .......... A61M 2210/0662; A61M 27/00; A61B 17/3205; A61B 17/32053; A61B 17/1615; A61B 17/1604
See application file for complete search history.

(56) References Cited

U.S. PATENT DOCUMENTS

| | | | |
|---|---|---|---|
| 2010/0239112 A1 | 9/2010 | Howard et al. | |
| 2012/0150070 A1* | 6/2012 | Ryan | A61B 10/0283 604/164.04 |
| 2013/0338678 A1* | 12/2013 | Loushin | A61F 11/202 606/109 |
| 2014/0094733 A1* | 4/2014 | Clopp | A61F 2/18 604/8 |
| 2014/0228871 A1* | 8/2014 | Cohen | A61B 17/32053 606/170 |
| 2015/0290040 A1* | 10/2015 | Vaughan | A61F 11/202 606/109 |
| 2016/0045369 A1* | 2/2016 | Clopp | A61F 11/202 606/109 |
| 2017/0056043 A1* | 3/2017 | Jenkins | A61B 17/1688 |
| 2017/0209310 A1 | 7/2017 | Girotra et al. | |
| 2017/0367893 A1 | 12/2017 | Loushin et al. | |
| 2019/0192349 A1* | 6/2019 | Vaughan | A61B 17/3468 |

FOREIGN PATENT DOCUMENTS

| | | |
|---|---|---|
| KR | 10-2012-0037480 A | 4/2012 |
| KR | 10-1497755 B1 | 3/2015 |
| WO | 2008-036368 A2 | 3/2008 |
| WO | 2014-075949 A1 | 5/2014 |
| WO | 2016-025453 A1 | 2/2016 |

* cited by examiner (a)

(b)

(c)

(d)

OTITIS MEDIA TREATMENT INSTRUMENT

TECHNICAL FIELD

The present disclosure relates to an otitis media treatment instrument, and more particularly, to an otitis media treatment instrument capable of making the treatment of otitis media more smooth.

BACKGROUND ART

Otitis media is an inflammatory disease that occurs in the middle ear. Most of them recover by themselves, but in severe cases, treatment is necessary.

One of the ways to treat otitis media is to install a ventilation tube in the eardrum. Installation of the ventilation tube is made by incising the eardrum and inserting the ventilation tube in an incision part. Through the installed ventilation tube, an exudate caused by inflammation is discharged, and the pressure between the middle ear and the outer ear is adjusted.

An instrument for installing the ventilation tube in the eardrum usually has a tubular front end portion, and during the process of incising the eardrum with the instrument, the ventilation tube is located inside the front end portion and is fixed by a frictional force with the inner circumferential surface of the front end portion or a frictional force with an outer circumferential surface of a rod-type member located inside the front end portion.

However, because the ventilation tube is not reliably fixed by frictional forces such as the ventilation tube and the inner circumferential surface of the front end portion, there is a problem that the ventilation tube is detached from the instrument before insertion of the ventilation tube into the incision of the eardrum.

DESCRIPTION OF EMBODIMENTS

Technical Problem

Provided is an otitis media treatment instrument, whereby a ventilation tube is reliably fixed to the otitis media treatment instrument so that the treatment of otitis media may be smoothly performed.

The problems to be solved by the present disclosure are not limited to the above-described problems, and other unmentioned problems will be clearly understood by those of ordinary skill in the art from the following description.

Solution to Problem

According to an aspect of the present disclosure, an otitis media treatment instrument having a ventilation tube installed thereon, the otitis media treatment instrument includes a cutting sheath which is configured in a tube shape, and which has an inner diameter larger than the outer diameter of the ventilation tube, and a suction pipe formed to be able to move relative to the cutting sheath inside the cutting sheath along the longitudinal direction of the cutting sheath, the suction pipe having, on the front end portion thereof, an insertion portion having an outer diameter smaller than the inner diameter of the ventilation tube and having a fixing portion which extends toward the front end of the insertion portion, and which has an outer diameter larger than the inner diameter of the ventilation tube.

A protrusion may be formed on an outer circumferential surface of the suction pipe and may protrude from a rear end position of the insertion portion.

An outer diameter of the suction pipe may be the same as an inner diameter of the cutting sheath at the rear end position of the insertion portion.

A front end portion of the cutting sheath may be sharply formed.

A front end portion of the cutting sheath may be formed in a spiral shape.

Advantageous Effects of Disclosure

Because, when otitis media is treated by using an otitis media instrument according to the disclosure, a ventilation tube cannot be easily detached from the instrument, the treatment can be prevented from stopping due to detachment of the ventilation tube or damage to parts other than those requiring treatment can be prevented while the instrument is moved to a position of the eardrum or the eardrum is incised.

In addition, the incision of the eardrum can be made easier.

MODE OF DISCLOSURE

Hereinafter, specific embodiments of the present disclosure will be described in detail with reference to the drawings.

Figure 1:
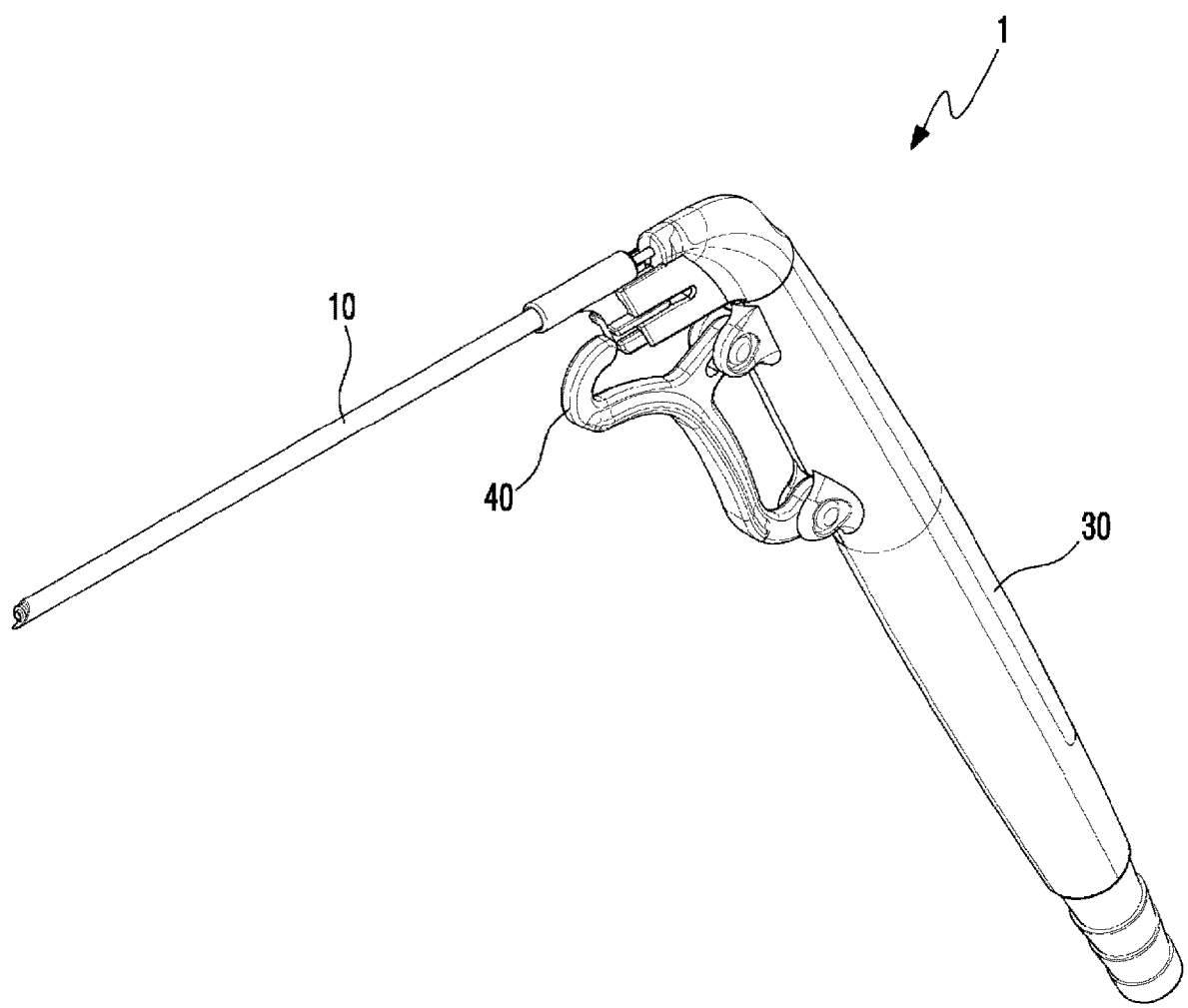
FIG. 1 is an overall perspective view of an otitis media treatment instrument according to the present disclosure.
Figure 2:
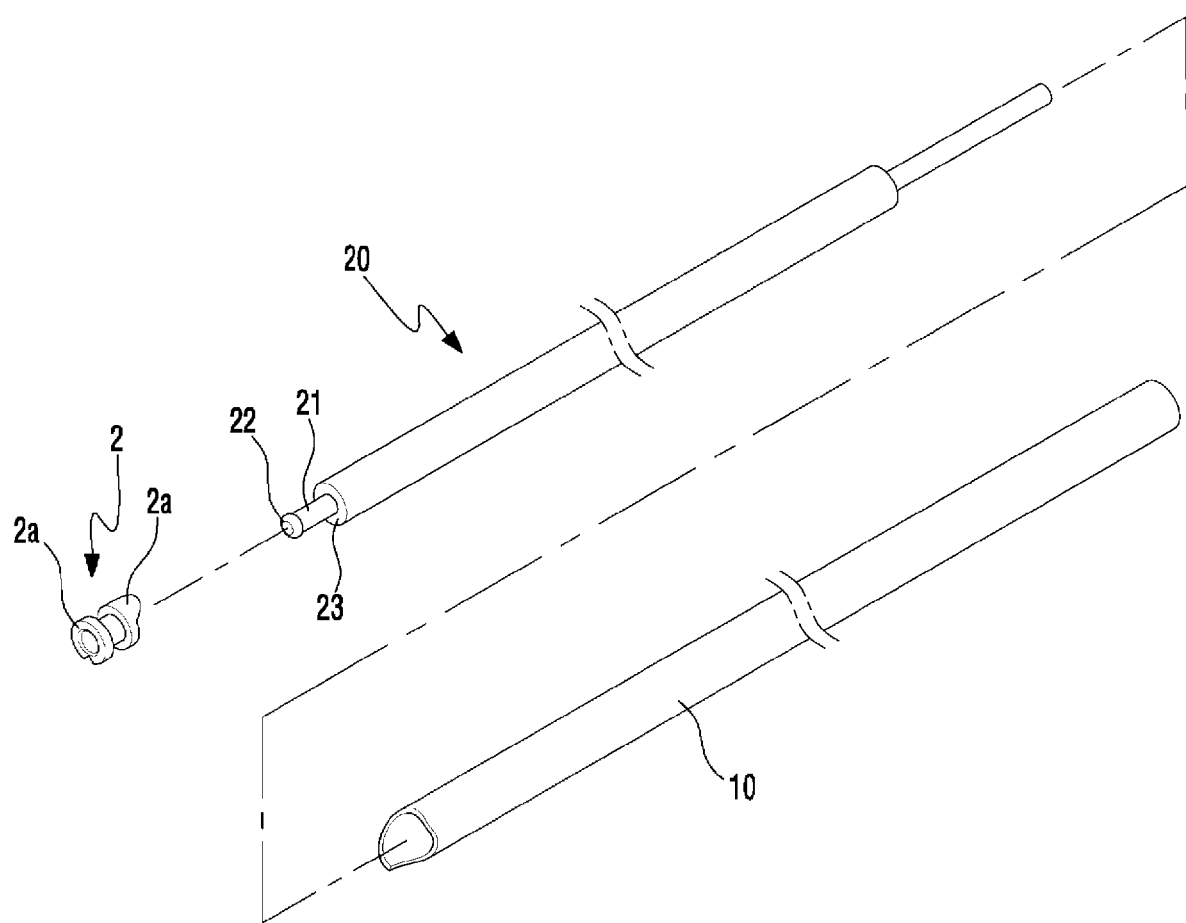
FIG. 2 is a partial exploded perspective view of the otitis media treatment instrument according to the present disclosure.
Figure 3:
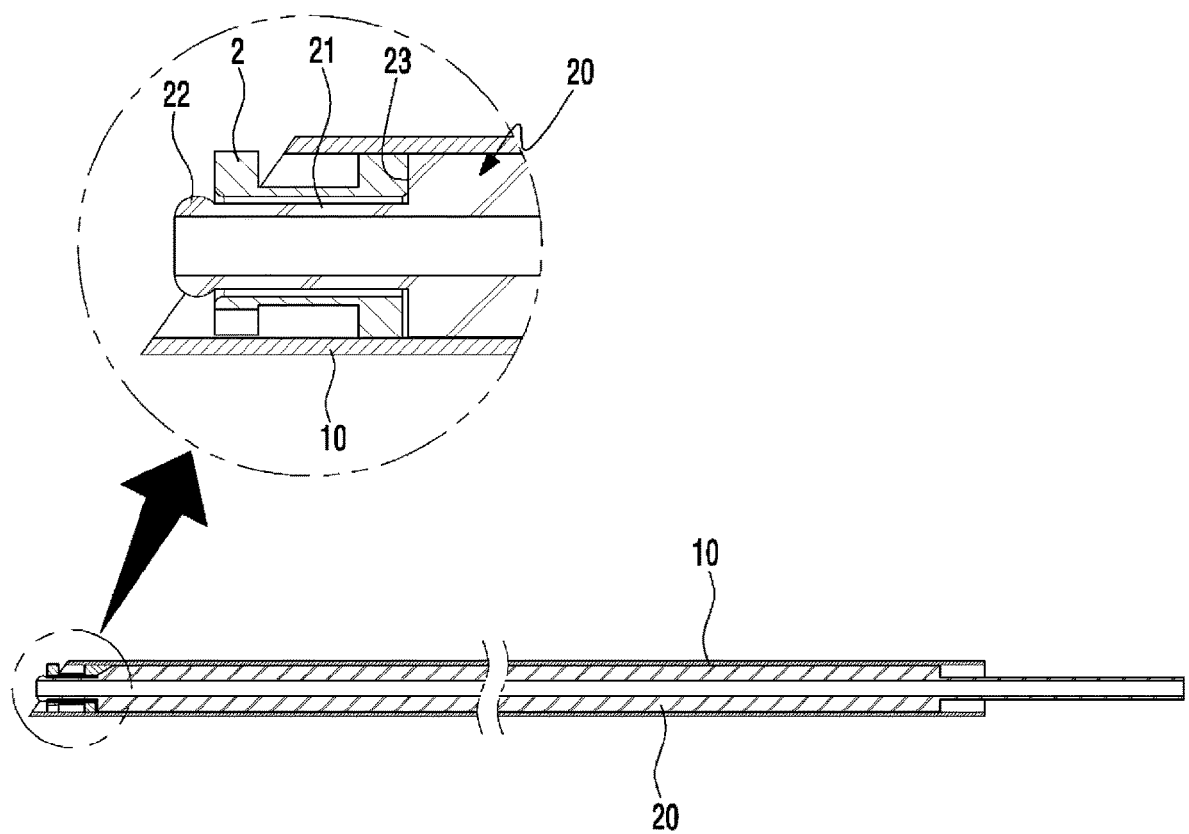
FIG. 3 is a partial cross-sectional view of the otitis media treatment instrument according to the present disclosure.

An overall perspective view of the otitis treatment instrument 1 according to the present disclosure is shown in FIG. 1, and a partial exploded perspective view of a front end portion of the otitis treatment instrument 1 according to the present disclosure is shown in FIG. 2. A partial cross-sectional view of the front end portion of the otitis treatment instrument is shown in FIG. 3.

In the treatment of otitis media, the otitis media treatment instrument 1 according to the present disclosure largely plays a role of incising the eardrum and installing a ventilation tube 2 at the incised position of the eardrum.

The otitis media treatment instrument 1 according to the present disclosure includes a cutting sheath 10 and a suction pipe 20.

The cutting sheath 10 may be a part forming the appearance of the front end portion of the otitis media treatment instrument 1 and may be configured in a long tube shape. An inner diameter of the cutting sheath 10 may be larger than an outer diameter of the ventilation tube 2 so that the ventilation tube 2 may be inserted into the cutting sheath 10. The eardrum may be incised through the front end portion of the cutting sheath 10.

The suction pipe 20 may be located inside the cutting sheath 10 and may be configured in a long tube shape. The suction pipe 20 may move relative to the cutting sheath 10 in the longitudinal direction of the cutting sheath 10 while a front end portion of the suction pipe 20 may protrude out of the front end portion of the cutting sheath 10 or be inserted into the cutting sheath 10. The suction pipe 20 is able to move relative to the cutting sheath 10. However, the cutting sheath 10 may move so that the relative position of the cutting sheath 10 to the suction pipe 20 may be changed. The exudate in the middle ear may be sucked and removed through the suction pipe 20.

An insertion portion 21 and a fixing portion 22 are provided on the front end portion of the suction pipe 20. The outer diameter of the insertion portion 21 may be smaller than the inner diameter of the ventilation tube 2, and the fixing portion 22 may extend toward a front end of the insertion portion 21, and the outer diameter of the fixing portion 22 may be larger than the inner diameter of the ventilation tube 2. The ventilation tube 2 may be maintained in a fixed state in the cutting sheath 10 by using the insertion portion 21 and the fixing portion 22. That is, when the ventilation tube 2 is located inside the cutting sheath 10, the ventilation tube 2 may be inserted into the front end portion of the suction pipe 20. Because the fixing portion 22 has an outer diameter larger than the inner diameter of the ventilation tube 2, the ventilation tube 2 may be prevented from being detached from the insertion portion 21.

In this way, in the otitis media treatment instrument 1 according to the present disclosure, because the ventilation tube 2 cannot be easily detached from the instrument, the treatment may be prevented from stopping due to detachment of the ventilation tube 2 or damage to parts other than those requiring treatment may be prevented while the instrument is moved to the eardrum or the eardrum is incised by the cutting sheath 10.

A protrusion 23 may be formed on an outer circumferential surface of the suction pipe 20. The protrusion 23 may protrude from a rear end position of the insertion portion 21.

The protrusion 23 may prevent the ventilation tube 2 inserted into the insertion portion 21 from moving to the rear end of the insertion portion 21, so that the ventilation tube 2 may be fixed to a certain position of the suction pipe 20. Thus, when the ventilation tube 2 is inserted into the incision part of the eardrum while moving the instrument, the ventilation tube 2 may be inserted into a correct position.

The outer diameter of the suction pipe 20 may be substantially the same as the inner diameter of the cutting sheath 10 at the rear end position of the insertion portion 21.

In this case, when the suction pipe 20 moves inside the cutting sheath 10, the suction pipe 20 may accurately move only in the longitudinal direction of the cutting sheath 10 without shaking in the radial direction of the cutting sheath 10 so that the accuracy of control of the suction pipe 20 may be prevented from being lowered.

Because, when the outer diameter of the suction pipe 20 is exactly the same as the inner diameter of the cutting sheath 10, it may be difficult that the suction pipe 20 moves inside the cutting sheath 10, the outer diameter of the suction pipe 20 and the inner diameter of the cutting sheath 10 may be almost the same, but the outer diameter of the suction pipe 20 may be slightly smaller than the inner diameter of the cutting sheath 10.

The front end portion of the cutting sheath 10 may be sharply formed.

As described above, the cutting sheath 10 serves to incise the eardrum. Thus, when the front end portion of the cutting sheath 10 is sharply formed, the incision of the eardrum may be more easily performed.

The front end portion of the cutting sheath 10 may be formed in a spiral shape.

Through the spiral front end portion of the cutting sheath 10, the eardrum may be drilled like a drill bit. That is, when the cutting sheath 10 is rotated in a state where the front end portion of the cutting sheath 10 is in contact with the eardrum, an almost circular incision part may be formed in the eardrum.

The otitis media treatment instrument 1 according to the present disclosure may further include a handle 30 connected to the cutting sheath 10 and a rear end of the suction pipe 20, a moving unit 40 for moving the suction pipe 20 relative to the cutting sheath 10, and a suction unit (not shown) that enables the suction pipe 20 to have a suction force, in addition to the configurations described above.

Figure 4:
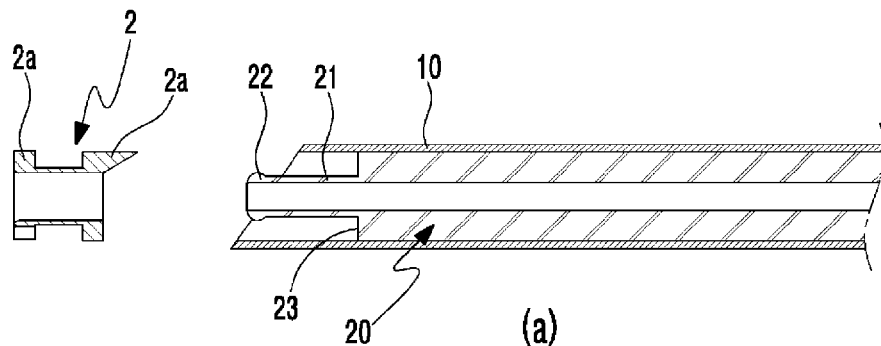
FIGS. 4 and 5 are explanatory diagrams illustrating a method of using the otitis media treatment instrument according to the present disclosure.
Figure 4:
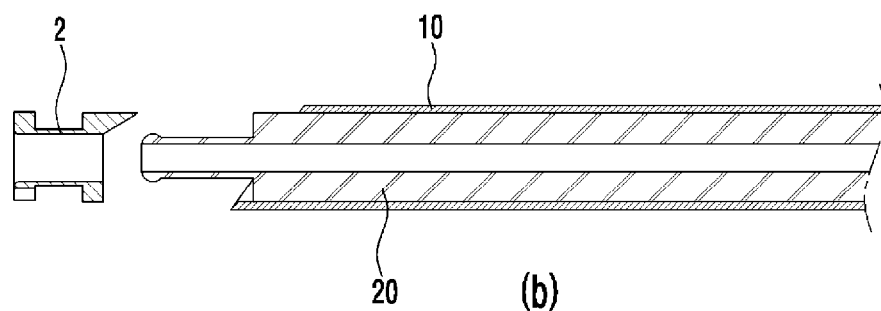
Figure 4:
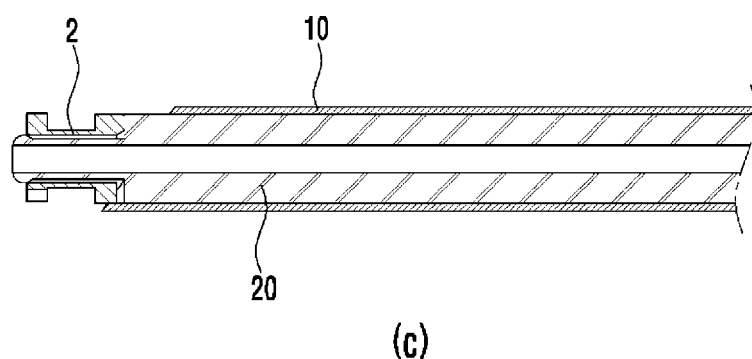
Figure 4:
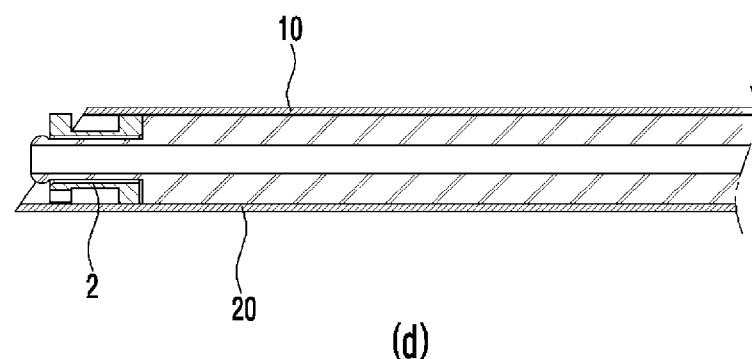
Figure 5:
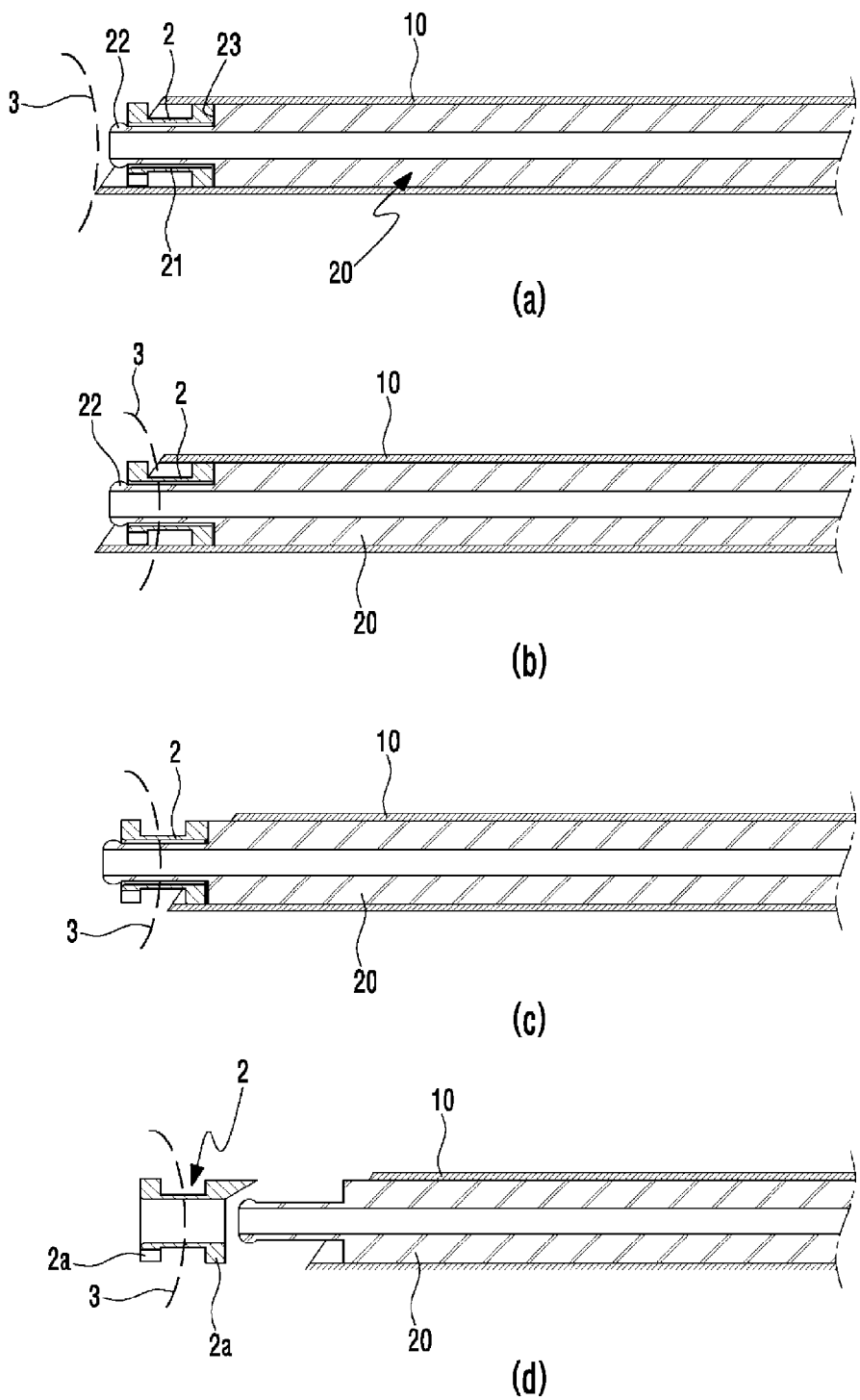

The otitis media treatment instrument 1 described above is used by the following method. FIGS. 4 and 5 are explanatory diagrams illustrating a method of using the otitis media treatment instrument. FIG. 4 illustrates an operation state of the otitis media treatment instrument in preparation for treatment, and FIG. 5 illustrates an operation state of the otitis media treatment instrument during the treatment.

The suction pipe 20 in a basic state may be located inside the cutting sheath 10, as shown in (a) of FIG. 4, and when the ventilation tube 2 is inserted into the suction pipe 20, as shown in (b) of FIG. 4, the moving unit 40 may be operated so that the front end portion of the suction pipe 20 may protrude to the outside of the cutting sheath 10. When the ventilation tube 2 is fixed to the suction pipe 20, the ventilation tube 2 may be inserted into the suction pipe 20 until the front end portion of the ventilation tube 2 reaches the rear end position of the fixing portion 22, as shown in (c) of FIG. 4, so that the ventilation tube 2 may not be easily detached from the suction pipe 20 by using the fixing portion 22 having an outer diameter larger than the inner diameter of the ventilation tube 2. When the operation of the moving unit 40 is released, as shown in (d) of FIG. 4, the suction pipe 20 may move into the cutting sheath 10, while the ventilation tube 2 may move into the cutting sheath 10 together. This completes the preparation of treatment by the otitis media treatment instrument according to the present disclosure.

When the treatment is performed by using the instrument in a state where the ventilation tube 2 is fixed, firstly, as shown in (a) of FIG. 5, the eardrum 3 is incised through the front end portion of the cutting sheath 10. The front end portion of the cutting sheath 10 may be sharply or spirally formed so that the eardrum 3 may be easily incised. The suction pipe 20 and the ventilation tube 2 may maintain a state located inside the cutting sheath 10 so that the suction pipe 20 or the ventilation tube 2 does not interfere with the operation during the incising operation of the eardrum 3. When the incision of the eardrum 3 is completed, the cutting sheath 10 may be inserted into the incision part, as shown in (b) of FIG. 5. In this case, the suction pipe 20 and the ventilation tube 2 located inside the cutting sheath 10 may be inserted into the incision part of the eardrum 3 together.

The moving unit 40 may be operated so that the cutting sheath 10 may be removed from the incision part of the eardrum 3 and positions of the suction pipe 20 and the ventilation tube 2 fixed to the suction pipe 20 may be maintained in the incision part of the eardrum 3, as shown in (c) of FIG. 5. Through the suction pipe 20 protruding to the outside of the cutting sheath 10, the exudate may be sucked and removed. The ventilation tube 2 located outside among the suction pipe 20 and the ventilation tube 2 may be in contact with the eardrum 3 and caught by the eardrum 3.

As shown in (d) of FIG. 5, when the otitis media treatment instrument according to the present disclosure may be retreated and removed from the eardrum 3, the suction pipe 20 and the ventilation tube 2 may be separated by the force of the ventilation tube 2 being caught by the eardrum 3. A portion 2a protruding from both ends in the longitudinal direction may be formed on the outer circumferential surface of the ventilation tube 2, as shown in FIG. 5, etc., so that the ventilation tube 2 may be more firmly fixed to the eardrum 3 by the protruding portion. The remaining or additionally-generated exudate may be discharged by the ventilation tube 2 that remains in the eardrum 3, and pressure between the middle ear and the outer ear may be adjusted.

The scope of the right of the present disclosure is not limited to the above-described embodiments but may be implemented in embodiments of various shapes within the attached claims. One or more embodiments will be understood by those of ordinary skill in the art that various changes in form and details may be made therein without departing from the spirit and scope as defined by the following claims.

The invention claimed is:

1. An otitis media treatment instrument installing a ventilation tube, the otitis media treatment instrument comprising:
    a cutting sheath configured in a tube shape, the cutting sheath having an inner diameter larger than an outer diameter of the ventilation tube; and
    a suction pipe configured to move relative to the cutting sheath inside the cutting sheath along a longitudinal direction of the cutting sheath, the suction pipe having, on a front end portion thereof, an insertion portion having an outer diameter smaller than an inner diameter of the ventilation tube and the suction pipe having a fixing portion, which extends toward a front end of the insertion portion and has an outer diameter larger than the inner diameter of the ventilation tube,
    wherein the suction pipe has a protrusion which protrudes from a rear end of the insertion portion of the suction pipe,
    wherein the ventilation tube is configured to be coupled to the insertion portion of the suction pipe, and
    wherein the ventilation tube is insertable into an eardrum by moving the suction pipe while one end of the ventilation tube is supported by the protrusion of the suction pipe, such that the suction pipe is configured to suck out an exudate from a middle ear through the suction pipe by way of the insertable ventilation tube.

2. The otitis media treatment instrument of claim 1, wherein an outer diameter of the suction pipe is the same as the inner diameter of the cutting sheath at the rear end of the insertion portion of the suction pipe.

3. The otitis media treatment instrument of claim 1, wherein a front end of the cutting sheath is sharply formed.

4. The otitis media treatment instrument of claim 1, wherein a front end of the cutting sheath is formed in a spiral shape.

* * * * *